(12) United States Patent
Fang

(10) Patent No.: US 10,299,727 B2
(45) Date of Patent: May 28, 2019

(54) CORONARY SINUS INSPIRATION CATHETER

(71) Applicant: Shengxian Fang, Guangdong (CN)

(72) Inventor: Shengxian Fang, Guangdong (CN)

( * ) Notice: Subject to any disclaimer, the term of this patent is extended or adjusted under 35 U.S.C. 154(b) by 349 days.

(21) Appl. No.: 15/238,780

(22) Filed: Aug. 17, 2016

(65) Prior Publication Data

US 2017/0251977 A1   Sep. 7, 2017

(30) Foreign Application Priority Data

Mar. 3, 2016   (CN) .......................... 2016 1 0120402

(51) Int. Cl.
   *A61B 5/00*   (2006.01)
   *A61B 5/15*   (2006.01)
   *A61M 25/00*  (2006.01)
   *A61M 25/01*  (2006.01)

(52) U.S. Cl.
   CPC ........ *A61B 5/6855* (2013.01); *A61B 5/15003* (2013.01); *A61B 5/150015* (2013.01); *A61B 5/150099* (2013.01); *A61B 5/150992* (2013.01); *A61M 25/0041* (2013.01); *A61M 25/0068* (2013.01); *A61M 25/007* (2013.01); *A61M 25/0054* (2013.01); *A61M 25/0108* (2013.01); *A61M 2025/0073* (2013.01); *A61M 2210/125* (2013.01)

(58) Field of Classification Search
   CPC ............ A61B 5/6855; A61B 5/150015; A61B 5/15003; A61B 5/150099; A61B 5/150992; A61M 25/0041; A61M 25/0068

USPC .......................................................... 600/581
See application file for complete search history.

(56) References Cited

U.S. PATENT DOCUMENTS

| | | | | |
|---|---|---|---|---|
| 5,423,772 A * | 6/1995 | Lurie | ................ | A61M 25/0041 600/374 |
| 6,090,084 A * | 7/2000 | Hassett | ................ | A61B 5/0422 600/434 |
| 6,277,107 B1 * | 8/2001 | Lurie | ................ | A61M 25/0041 604/523 |
| 2005/0080398 A1 * | 4/2005 | Markel | ............. | A61M 25/0014 604/508 |
| 2008/0255447 A1 * | 10/2008 | Bourang | ............. | A61M 31/005 600/434 |

* cited by examiner

*Primary Examiner* — Daniel L Cerioni

(57) ABSTRACT

The present invention provides a coronary sinus inspiration catheter comprising a catheter head section and an extension tube, which are hollow tubular structures, the catheter head section and a distal section of the extension tube are substantially arc-shaped, the catheter head section comprises an arc section and a bend section, and its length is about 4-10 cm, the distal end is small (3-6 F) and the tube diameter of the catheter head section increase gradually toward the proximal end (6-12 F), the catheter head section is bent at a 15-45° angle at the position which has a distance of 0.5-1.5 cm from the distal end, the bend section is a straight or slightly arc-shaped structure. The catheter head section is provided with an end hole and a plurality of side holes, and is equidistantly provided with radiopaque markers from the distal end to the proximal end.

9 Claims, 1 Drawing Sheet

CORONARY SINUS INSPIRATION CATHETER

The present invention belongs to the field of medical devices, in particular to a new coronary sinus inspiration catheter.

BACKGROUND

Coronary sinus is an extending expansion part of the great cardiac vein and locates in the left atrioventricular sulcus (coronary sulcus) of the heart, the coronary sinus collects venous blood of the heart back to the right atrium. In research and clinical work, sometimes the blood in the coronary sinus of the heart needs to be sucked out of the body for analysis or processing, this needs to design a special coronary sinus inspiration catheter.

SUMMARY

The present invention discloses a new type of catheter—coronary sinus inspiration catheter with a hollow structure which is used to suck the blood in the coronary sinus out of the body. The catheter can meet requirements of sucking the blood in the coronary sinus during the research or clinical work.

The present invention uses the following technical solution to solve the above technical problem:

A coronary sinus inspiration catheter comprises a catheter head section and an extension tube, the catheter head section and the extension tube are hollow tubular structures, the catheter head section and a distal section of the extension tube are substantially arc-shaped, the catheter head section comprises a proximal end and a distal end, the extension tube extends from the proximal end of the catheter head section and a diameter of the extension tube is consistent, the catheter head section comprises an arc section and a bend section, the arc section is disposed at the proximal end of the catheter head section and is arc-shaped, the bend section is disposed at the distal end of the catheter head section, the bend section is a straight or slightly arc-shaped structure; the bend section is connected to the arc section, and the bend section extends toward the center of an arc of the arc section; the catheter head section is provided with a flow communication hole.

Further more, the diameter of the catheter head section decreases gradually from the proximal end to the distal end.

Further more, the diameter of the proximal end of the catheter head section is 6-12 F, and the diameter of the distal end of the catheter head section is 3-6 F.

Further more, the catheter head section has a total length of 4-10 cm, the bend section has the length of 0.5-1.5 cm, and the arc section has the length of 3.5-6.5 cm.

Further more, the arc section in a free state has a radius of curvature of 50-120 mm.

Further more, a connection position between the bend section and the arc section is a bend point, a tangential at the bend point of the arc section and the bend section form an angle of 15°-45°.

Further more, the flow communication hole comprises an end hole and a plurality of side holes, the end hole is positioned at the end surface of the distal end of the catheter head section, the side holes are disposed on the wall of the catheter head section.

Further more, a sum of the areas of the end hole and the side holes is larger than a cross-sectional area of the proximal end of the catheter head section, and less than 1.5 times of the cross-sectional area of the proximal end of the catheter head section.

Further more, the catheter head section is equidistantly provided with radiopaque markers from the distal end to the proximal end.

Further more, the radiopaque markers are disposed on the wall of the catheter head section in an annular strip manner, a distance between centers of two radiopaque markers is 1 cm; the radiopaque marker has a width of 0.5-2 mm.

Further more, the coronary sinus inspiration catheter further comprises an extracorporeal connector to connect to other devices, the extracorporeal connector is connected to the extension tube.

Further more, wherein the catheter head section and the extension tube are formed integrately, and the catheter head section and the extension tube are made of a soft material having elasticity, the coronary sinus inspiration catheter has characteristics of catheters, and has smooth surface and inner cavity, and the wall thereof is provided with a support material.

The coronary sinus inspiration catheter comprises catheter head section configured as an arc-shaped structure, and the diameter of proximal end thereof is small and the distal end thereof is larger, which is consistent with the shape of the coronary sinus, and facilitates the catheter head section to extend inside the coronary sinus without hurting the vascular wall; arranging the end hole and side holes has the advantages of uniform inspiration, high inspiration efficiency.

The distal portion of extension section of the coronary sinus inspiration catheter also has a substantive arc-shaped structure and is connected with the catheter head section, such that the catheter head section can get access to the ostium of the coronary sinus more easily; the catheter head section is bent at a certain angle, so that the catheter head section can enter the ostium of the coronary sinus more easily.

Figure 1:
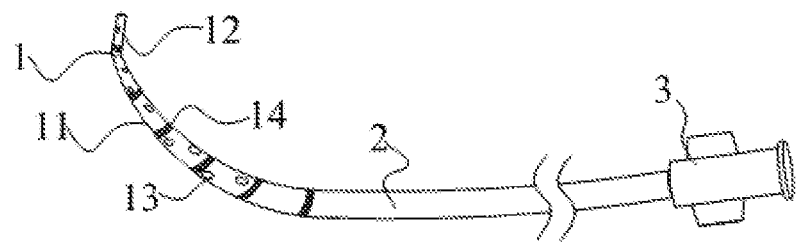
FIG. 1 is a schematic structure diagram of a coronary sinus inspiration catheter of the present invention.

Reference numbers in the drawings are as follow:

1 catheter head section; 11 arc section; 12 bend section; 13 flow communication hole; 131 side hole; 132 end hole; 14 radiopaque marker; 2 extension tube; 3 extracorporeal connector.

DESCRIPTION OF EMBODIMENTS

To make the technical problem, technical solutions, and advantages of the present invention clearer, the following further describes the present invention in detail with reference to the accompanying drawings and embodiments. It should be understood that the specific embodiment described herein is merely used to explain the present invention but is not used to limit the present invention.

In the description of the present invention it should be understood that terms "length", "thickness", "upper", "lower", "front", "back", "top", "bottom", "inner", "extracorporeal" and the like indicative of azimuth and position relationships based on the azimuth and position relationships as illustrated in the drawings are merely for briefly describing the present invention or simplifying the description, rather than denoting or implying that the denoted apparatuses or elements need to be positioned at specific azimuths and constructed and operated with the specific azimuths, but shall not be construed as limitations to the invention. Unless stated otherwise, the term "a plurality of" means two or more in the description of the present invention.

In the description of the present invention, It is to be noted that, unless explicitly regulated and restricted otherwise, the terms "mount", "connect", "couple" should be understood in a broad sense, for example, the terms may denote a fixed connection, a detachable connection, or an integral connection; the relative components may be coupled directly, may also be indirectly coupled through intermediate parts, or may be a internal communication therebetween. The skilled person in this art can appreciate the specific meaning in the present invention of the above terms according to specific circumstances.

As shown in FIG. 1, the present invention discloses a coronary sinus inspiration catheter, the coronary sinus inspiration catheter comprises a catheter head section 1 and an extension tube 2. The catheter head section 1 and the extension tube 2 are hollow tubular structures. The catheter head section 1 and a distal section of the extension tube 2 are substantially arc-shaped. The distal end of the extension tube 2 is connected to the catheter head section 1. The catheter head section 1 comprises a proximal end and a distal end, the proximal end is connected to the extension tube 2, that is, the catheter head section 1 is connected to the extension tube 2. The catheter head section 1 is used to collect the blood in the coronary sinus, the blood flows into the catheter head section 1 and is guided out of the body though the extension tube 2.

The catheter head section 1 comprises an arc section 11 and a bend section 12, the arc section 11 is disposed at the proximal end of the catheter head section and is arc-shaped, the bend section 12 is disposed at the distal end of the catheter head section, the bend section 12 is a straight or slightly arc-shaped structure; the bend section 12 is connected to the arc section 11, and the bend section 12 extends toward the center of an arc of the arc section. The bend section 12 is to incline the distal end of the catheter head section at a certain angle, such that the catheter head section 1 can be inserted into the coronary sinus easily trough the bend section 12 when the catheter head section 1 is near the coronary sinus, then the catheter head section enters the coronary sinus. The arc section 11 of the catheter head section 1 is to simulate the internal morphology of the coronary sinus. Since the inside of the coronary sinus is arc-shaped, the arc section 11 facilitate the extension of the catheter head section 1 in the coronary sinus, such that the catheter can be placed deeper in the coronary sinus to collect the in the coronary sinus without hurting the vessel wall.

The distal section of the extension tube is also substantive arc-shaped and is connected with the catheter head section, such the catheter head section can get access to the ostium of the coronary sinus easily. The catheter head section is bent at a certain angle, so that the catheter head section can enter the ostium of the coronary sinus more easily.

The catheter head section 1 is provided with radiopaque markers 14. Because the coronary sinus inspiration catheter is inserted into the coronary sinus under the X-rays, disposing radiopaque markers 14 on the catheter head section 1 will help the operator to know the position of the coronary sinus inspiration catheter in the coronary sinus.

As a preferred embodiment of the present invention, the radiopaque markers 14 are disposed on the wall of the catheter head section in an annular strip manner. The radiopaque markers 14 are equidistantly disposed along the catheter head section from the distal end to the proximal end, a distance between centers of two radiopaque markers is 1 cm, the radiopaque marker has a width of 0.5-2 mm. However, the distance between the radiopaque marker near the distal end and the nearest radiopaque marker thereof may be less than 1 cm based on the different lengths of the catheter head section. It should be noted that the radiopaque markers may be formed by coating radiopaque layers on the outer wall of the catheter head section, or may be formed from other opaque material. On the other hand, in the present invention, the radiopaque markers are arranged in an annular strip manner to improve the imaging discrimination under the X-rays. The skilled person in the art may also select other arrangement according to different requirements, such as a grid-like arrangement, which is in the protection scope of the present invention.

The catheter head section 1 is provided with a flow communication hole 13, the flow communication hole comprises an end hole 132 and side holes 131. The flow communication hole 13 communicates inside and outside of the catheter head section, the blood flows into the catheter head section 1 through the flow communication hole 13.

As a preferred embodiment of the present invention, the arc section 11 is arc-shaped, the arc section in a free state has a radius of curvature of 50-120 mm, more preferably 80-90 mm. It should be noted that, the radius of curvature is the radius of curvature of the arc section 11 when the coronary sinus inspiration catheter is in a free state, the catheter head section 1 has a certain elasticity of curvature and extension, such that the radius of curvature of the catheter head section 1 may increase or decrease correspondingly when the catheter head section 1 is in the coronary sinus, to help catheter head section 1 moving forward along the vessel. After entering the right atrium the catheter head section 1 and the extension tube may be recovered to the arc in the free state, the coronary sinus inspiration catheter is rotated such that the catheter head section 1 is pointed to the coronary sinus ostium and the bend section 12 guides the catheter head section 1 into the coronary sinus. If the radius of curvature is too big or too small, it is not conducive to push the coronary sinus inspiration catheter to the deeper position, and is easy to hurt the vessel. Therefore, within the scope of radius of curvature disclosed in the present invention, the coronary sinus inspiration catheter may obtain a best operating result.

As another embodiment of the present invention, the arc section 11 is not limited to the arc with one radius of curvature, and may be an arc of an oval, or may be the combination of arcs with different curvatures.

In this embodiment, the total length of the catheter head section is preferably 4-10 cm, the length of the arc section 11 is preferably 3.5-6.5 cm. In the present invention, the length of the arc section 11 is selected according to the length of the human body the coronary sinus, such that the catheter head section 1 can be consistent with the length and curvature of the coronary sinus when the catheter head section 1 is in the coronary sinus. Since there are some differences between the human bodies, the length of 3.5-6.5 cm is selected as a preferred length of the arc section in the present invention. The skilled person in the art can also choose other length based on the special nature of the patient's condition, the other equivalent alternative technical solution should also be included within the scope of the present invention.

In the present embodiment, the bend section 12 is a straight or slightly arc-shaped structure, and has a length of 0.5-1.5 cm. In particular embodiments, the bend section should not be too long.

As a preferred embodiment of the present invention, the bend section 12 is connected with the arc section 11, the bend section 12 extends from the arc section 11 and toward the center of an arc of the arc section 11. A connection position between the bend section 12 and the arc section 11 is a bend point, a tangential at the bend point of the arc section and the bend section form an angle of 15°-45°, such that the distal end of the catheter head section 1 is bent toward the inner of the curvature of the arc section 11, to help the catheter head section 1 enter into the coronary sinus ostium. If the angle between the tangentials at the bend point of the arc section and the bend section is too large or too small, it is not easy for the catheter head section 1 to enter the coronary sinus ostium, the large angle is not conducive to advance the catheter in the vessel, and it is easy to hurt the coronary vein.

Figure 2:
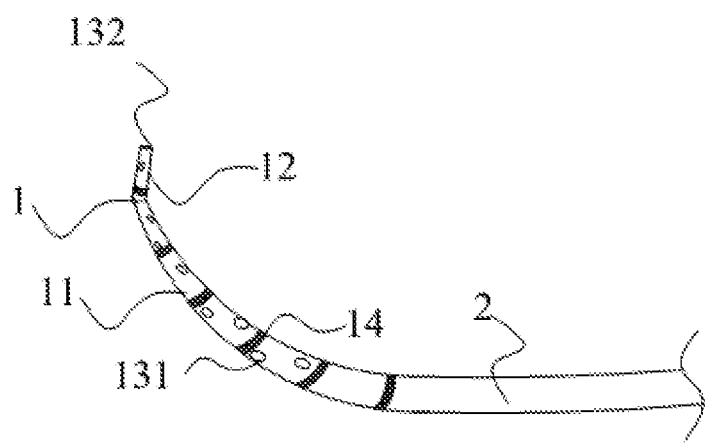
FIG. 2 is a schematic structure diagram of a catheter head section of the present invention.

As shown in FIG. 2, the catheter head section 1 is further provided with a flow communication hole 13, the flow communication hole 13 comprises an end hole 132 and side holes 131. The end hole 132 is positioned at the end surface of the distal end of the catheter head section 1, the side holes 131 are disposed on the wall of the catheter head section. Since the coronary sinus has a number of branches, such as the great cardiac vein, middle cardiac vein, small cardiac veins and so on. The venous blood flows from the cardiac veins to the coronary sinus, and the catheter head section is not only provided with the end hole 132 at the distal end, but also is provided with side holes 131 on the wall. When the catheter head section 1 is in the coronary sinus, the end hole 132 faces to the great cardiac vein and the side holes are distributed along inlets of the branches, through the cooperation of the end hole 132 and the side holes 131, the venous blood in different places of the coronary sinus may be sucked simultaneously, thereby improving the uniformity and efficiency of sucking blood. On the other hand, the plurality of communication holes 13 can effectively avoid clogging the catheter head section 1, when some hole is blocked, the blood may be sucked through other holes, such that the catheter head section 1 may complete the inspiration successfully.

In this embodiment, a sum of the areas of the end hole and the side holes is larger than a cross-sectional area of the proximal end of the catheter head section, the holes are designed mainly on account of the resistance of the holes to blood flow, which helps to improve the inspiration speed of the blood. Meanwhile, the sum of the areas of the end hole and the side holes is less than 1.5 times of the cross-sectional area of the proximal end of the catheter head section, to avoid an excessive sucking speed resulting in the right atrium blood being sucked out.

The diameter of the catheter head section 1 decreases gradually from the proximal end to the distal end, such structure is similar to the coronary sinus of the human body, it is conducive to insert the catheter head section 1 more deeply into the coronary sinus, such that the blood sample deep in the coronary sinus may be collected while without sucking the right atrium blood, thereby improving the accuracy of collecting blood sample.

Specifically, the diameter of the proximal end of the catheter head section is 6-12 F, and the diameter of the distal end of the catheter head section is 3-6 F. The diameter unit employed in the present invention is F, that is the abbreviation of the word "French" which can also be abbreviated as FR or Fr, 3F=1 mm.

Figure 3:
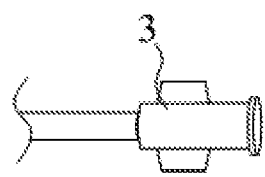
FIG. 3 is a schematic structure diagram of an extracorporeal connector of the present invention.

As shown FIGS. 1 and 3, the coronary sinus inspiration catheter also comprises an extracorporeal connector 3, the extracorporeal connector 3 is connected to the extension tube 2. And the extracorporeal connector 3 is connected to an extracorporeal instrument. The extracorporeal instrument may be a pressure extension tube, syringe, vacuum tube, vacuum pump and so on, and the extracorporeal instrument is used to form a negative pressure environment in the coronary sinus inspiration catheter, thereby sucking the blood in the coronary sinus through the coronary sinus inspiration catheter. The present invention doesn't limit the specific type of the extracorporeal connectors 3, those skilled in the art can select the extracorporeal connector according to actual requirements, and other extracorporeal connector allowing connection should also be included within the scope of the present invention.

The catheter head section 1 and the extension tube 2 are formed integrately, and the catheter head section 1 and the extension tube 2 are made of a soft material having elasticity, when the catheter head section 1 enters the coronary sinus, the catheter head section 1 can be advanced along the blood vessel. And a support material (such as steel mesh) is provided in the wall of the catheter to prevent fold and collapse. The coronary sinus inspiration catheter has characteristics of catheters, and has smooth surface and inner cavity, which can prevent adsorption and coagulation of the blood.

When using the coronary sinus inspiration catheter of the present invention for coronary sinus inspiration, the operation is as follow:

Step one: selecting a subclavian vein or right internal jugular vein as a puncture point, disinfecting locally, and puncturing the left subclavian vein or right internal jugular vein with needle;

Step two: inserting a guide wire through the core of the needle after a backflow blood is seen in the needle, fixing the guide wire, pulling out the needle, and then inserting a sheath through the guide wire, pulling out the guide wire and the core of the sheath, flushing with a heparin saline;

Step three: under the X-ray, inserting the coronary sinus inspiration catheter into the sheath and then passing the coronary sinus inspiration catheter through the sheath to get near the coronary sinus, rotating the coronary sinus inspiration catheter so that the catheter head section is pointed to the coronary sinus ostium, thereby guiding the catheter head section into the coronary sinus through the bend section.

Step four: fixing the catheter at the puncture point, connecting with an extracorporeal negative pressure device, turning on the negative pressure device to suck blood.

The following embodiments will further illustrate the present invention.

Embodiment 1

This embodiment is intended to illustrate the coronary sinus inspiration catheter disclosed by the present invention.

The coronary sinus inspiration catheter comprises a catheter head section and an extension tube. The catheter head section and the extension tube are hollow tubular structures. The catheter head section comprises a proximal end and a distal end, the proximal end is connected to the extension tube. The catheter head section comprises an arc section and a bend section, the arc section is disposed at the proximal end of the catheter head section and is arc-shaped, the bend section is disposed at the distal end of the catheter head section, the bend section is a straight or slightly arc-shaped structure.

The catheter head section is provided with radiopaque markers. The radiopaque markers are disposed on the outer wall of the catheter head section in an annular strip manner. The radiopaque markers are equidistantly disposed along the catheter head section from the distal end to the proximal end, a distance between centers of two radiopaque markers is 1 cm. However, the distance between the sixth radiopaque marker and the seventh radiopaque marker is 0.5 cm.

The catheter head section is provided with flow communication holes, the flow communication hole comprises an end hole and side holes. The end hole is positioned at the end surface of the distal end of the catheter head section, the side holes are disposed on the wall of the catheter head section. The sum of the areas of the end hole and the side holes is 1.2 times of the cross-sectional area of the proximal end of the catheter head section.

The diameters of the proximal end of the catheter head section and the extension tube are 6 F, the diameter of the catheter head section decreases gradually from the proximal end to the distal end, and the diameter of the distal end of the catheter head section is 4 F. The catheter head section has the length of 5.5 cm, the wall thickness of 0.1 mm. 6 side holes are disposed on the catheter head section and are spirally and equidistantly arranged from the distal end to the proximal end, there is no side hole from the distal end of the catheter head section to the position 5 mm away from the distal end of catheter head section, to prevent sucking the blood in the atrium, the side hole has the diameter of 0.6 mm.

The radius of curvature of the arc section is 80 mm.

The bend section is bent toward the center of an arc of the arc section, the bend section and the tangential of the arc section form an angle of 30°, the length of the bend section is 1 cm.

Embodiment 2

This embodiment is intended to illustrate the coronary sinus inspiration catheter disclosed by the present invention.

The coronary sinus inspiration catheter comprises a catheter head section and an extension tube. The catheter head section and the extension tube are hollow tubular structures. The catheter head section comprises a proximal end and a distal end, the proximal end is connected to the extension tube. The catheter head section comprises an arc section and a bend section, the arc section is disposed at the proximal end of the catheter head section and is arc-shaped, the bend section is disposed at the distal end of the catheter head section, the bend section is a straight or slightly arc-shaped structure.

The catheter head section is provided with radiopaque markers. The radiopaque markers are disposed on the outer wall of the catheter head section in an annular strip manner. The radiopaque markers are equidistantly disposed along the catheter head section from the distal end to the proximal end, a distance between centers of two radiopaque markers is 1 cm. However, the distance between the sixth radiopaque marker and the seventh radiopaque marker is 0.5 cm.

The catheter head section is provided with flow communication holes, the flow communication hole comprises an end hole and side holes. The end hole is positioned at the end surface of the distal end of the catheter head section, the side holes are disposed on the wall of the catheter head section. The sum of the areas of the end hole and the side holes is 1.43 times of the cross-sectional area of the proximal end of the catheter head section.

The diameters of the proximal end of the catheter head section and the extension tube are 6 F, the diameter of the catheter head section decreases gradually from the proximal end to the distal end, and the diameter of the distal end of the catheter head section is 4.5 F. The catheter head section has the length of 5.5 cm, the wall thickness of 0.1 mm. 6 side holes are disposed on the catheter head section and are spirally and equidistantly arranged from the distal end to the proximal end, there is no side hole from the distal end of the catheter head section to the position 5 mm away from the distal end of catheter head section, to prevent sucking the blood in the atrium, the side hole has the diameter of 0.7 mm.

The radius of curvature of the arc section is 70 mm.

The bend section is bent toward the center of an arc of the arc section, the bend section and the tangential of the arc section form an angle of 25°, the length of the bend section is 0.8 cm.

Embodiment 3

This embodiment is intended to illustrate the coronary sinus inspiration catheter disclosed by the present invention.

The coronary sinus inspiration catheter comprises a catheter head section and an extension tube. The catheter head section and the extension tube are hollow tubular structures. The catheter head section comprises a proximal end and a distal end, the proximal end is connected to the extension tube. The catheter head section comprises an arc section and a bend section, the arc section is disposed at the proximal end of the catheter head section and is arc-shaped, the bend section is disposed at the distal end of the catheter head section, the bend section is a straight or slightly arc-shaped structure.

The catheter head section is provided with radiopaque markers. The radiopaque markers are disposed on the outer wall of the catheter head section in an annular strip manner. The radiopaque markers are equidistantly disposed along the catheter head section from the distal end to the proximal end, a distance between centers of two radiopaque markers is 1 cm. However, the distance between the sixth radiopaque marker and the seventh radiopaque marker is 1 cm.

The catheter head section is provided with flow communication holes, the flow communication hole comprises an end hole and side holes. The end hole is positioned at the end surface of the distal end of the catheter head section, the side holes are disposed on the wall of the catheter head section. The sum of the areas of the end hole and the side holes is 1.38 times of the cross-sectional area of the proximal end of the catheter head section.

The diameters of the proximal end of the catheter head section and the extension tube are 7 F, the diameter of the catheter head section decreases gradually from the proximal end to the distal end, and the diameter of the distal end of the catheter head section is 4 F. The catheter head section has the length of 6 cm, the wall thickness of 0.1 mm. 7 side holes are disposed on the catheter head section and are spirally and equidistantly arranged from the distal end to the proximal end, there is no side hole from the distal end of the catheter head section to the position 5 mm away from the distal end of catheter head section, to prevent sucking the blood in the atrium, the side hole has the diameter of 0.8 mm.

The radius of curvature of the arc section is 70 mm.

The bend section is bent toward the center of an arc of the arc section, the bend section and the tangential of the arc section form an angle of 25°, the length of the bend section is 0.8 cm.

Embodiment 4

This embodiment is intended to illustrate the coronary sinus inspiration catheter disclosed by the present invention.

The coronary sinus inspiration catheter comprises a catheter head section and an extension tube. The catheter head section and the extension tube are hollow tubular structures. The catheter head section comprises a proximal end and a distal end, the proximal end is connected to the extension tube. The catheter head section comprises an arc section and a bend section, the arc section is disposed at the proximal end of the catheter head section and is arc-shaped, the bend section is disposed at the distal end of the catheter head section, the bend section is a straight or slightly arc-shaped structure.

The catheter head section is provided with radiopaque markers. The radiopaque markers are disposed on the outer wall of the catheter head section in an annular strip manner. The radiopaque markers are equidistantly disposed along the catheter head section from the distal end to the proximal end, a distance between centers of two radiopaque markers is 1 cm. However, the distance between the sixth radiopaque marker and the seventh radiopaque marker is 0.5 cm.

The catheter head section is provided with flow communication holes, the flow communication hole comprises an end hole and side holes. The end hole is positioned at the end surface of the distal end of the catheter head section, the side holes are disposed on the wall of the catheter head section. The sum of the areas of the end hole and the side holes is 1.44 times of the cross-sectional area of the proximal end of the catheter head section The diameters of the proximal end of the catheter head section and the extension tube are 7 F, the diameter of the catheter head section decreases gradually from the proximal end to the distal end, and the diameter of the distal end of the catheter head section is 4.5 F. The catheter head section has the length of 5.5 cm, the wall thickness of 0.1 mm. 6 side holes are disposed on the catheter head section and are spirally and equidistantly arranged from the distal end to the proximal end, there is no side hole from the distal end of the catheter head section to the position 5 mm away from the distal end of catheter head section, to prevent sucking the blood in the atrium, the side hole has the diameter of 0.9 mm.

The radius of curvature of the arc section is 65 mm.

The bend section is bent toward the center of an arc of the arc section, the bend section and the tangential of the arc section form an angle of 30°, the length of the bend section is 1 cm.

The foregoing descriptions are merely exemplary embodiment of the present invention, but are not intended to limit the present invention. Any modification, equivalent replacement, or improvement made without departing from the spirit and principle of the present invention shall fall within the protection scope of the present invention.

What is claimed is:

1. A coronary sinus inspiration catheter, wherein the coronary sinus inspiration catheter comprises a catheter head section and an extension tube, wherein the catheter head section and the extension tube are hollow tubular structures, the catheter head section and a distal section of the extension tube are substantially arc-shaped, the catheter head section comprises a proximal end and a distal end, the extension tube extends from the proximal end of the catheter head section and a diameter of the extension tube is consistent, the catheter head section comprises an arc section and a bend section, the arc section is disposed at the proximal end of the catheter head section and is arc-shaped, the bend section is disposed at the distal end of the catheter head section, the bend section is a straight or slightly arc-shaped structure; the bend section is connected to the arc section, and the bend section extends toward the center of an arc of the arc section; the catheter head section is provided with a flow communication hole, the diameter of the catheter head section decreases gradually from the proximal end to the distal end, the flow communication hole comprises an end hole and a plurality of side holes, the end hole is positioned at the end surface of the distal end of the catheter head section, the side holes are disposed on the wall of the catheter head section, a sum of the areas of the end hole and the side holes is larger than a cross-sectional area of the proximal end of the catheter head section, and less than 1.5 times of the cross-sectional area of the proximal end of the catheter head section.

2. The coronary sinus inspiration catheter of claim 1, wherein the diameter of the proximal end of the catheter head section is 6-12 F, and the diameter of the distal end of the catheter head section is 3-6 F.

3. The coronary sinus inspiration catheter of claim 1, wherein the catheter head section has a total length of 4-10 cm, the bend section has the length of 0.5-1.5 cm, the arc section has the length of 3.5-6.5 cm.

4. The coronary sinus inspiration catheter of claim 1, wherein the arc section in a free state has a radius of curvature of 50-120 mm.

5. The coronary sinus inspiration catheter of claim 1, wherein a connection position between the bend section and the arc section is a bend point, a tangential at the bend point of the arc section and the bend section form an angle of 15°-45°.

6. The coronary sinus inspiration catheter of claim 1, wherein the catheter head section is equidistantly provided with radiopaque markers from the distal end to the proximal end.

7. The coronary sinus inspiration catheter of claim 6, wherein the radiopaque markers are disposed on the wall of the catheter head section in an annular strip manner, a distance between centers of two radiopaque markers is 1 cm; the radiopaque marker has a width of 0.5-2 mm.

8. The coronary sinus inspiration catheter of claim 1, wherein the coronary sinus inspiration catheter further comprises an extracorporeal connector to connect to other devices, the extracorporeal connector is connected to the extension tube.

9. The coronary sinus inspiration catheter of claim 1, wherein the catheter head section and the extension tube are formed integrally, and the catheter head section and the extension tube are made of a soft material having elasticity, the coronary sinus catheter has smooth surface and inner cavity, and the wall thereof is provided with a support material.

* * * * *